(12) United States Patent
Naidu

(10) Patent No.: US 6,797,266 B2
(45) Date of Patent: Sep. 28, 2004

(54) **PROBIOTIC COMPOSITION CONTAINING *LACTOBACILLUS CASEI* STRAIN ATCC PTA-3945**

(75) Inventor: A. Satyanarayan Naidu, Diamond Bar, CA (US)

(73) Assignee: Probiohealth, Los Angeles, CA (US)

( * ) Notice: Subject to any disclaimer, the term of this patent is extended or adjusted under 35 U.S.C. 154(b) by 135 days.

(21) Appl. No.: 10/021,871

(22) Filed: Dec. 17, 2001

(65) Prior Publication Data

US 2002/0192202 A1 Dec. 19, 2002

Related U.S. Application Data

(60) Provisional application No. 60/256,528, filed on Dec. 18, 2000.

(51) Int. Cl.[7] ......................... A01N 63/00; C12N 1/00; C12N 1/20
(52) U.S. Cl. .................... 424/93.45; 424/93.4; 435/856
(58) Field of Search ............................ 424/93.4, 93.45; 435/856, 252.1, 252.9

(56) References Cited

U.S. PATENT DOCUMENTS

| | | |
|---|---|---|
| 3,957,974 A | 5/1976 | Hata |
| 4,210,672 A | 7/1980 | Hata |
| 4,314,995 A | 2/1982 | Hata et al. |
| 4,345,032 A | 8/1982 | Hata |
| 4,579,734 A | 4/1986 | Hata et al. |
| 4,839,281 A | 6/1989 | Gorbach et al. |
| 4,871,539 A | 10/1989 | Hata et al. |
| 4,879,238 A | 11/1989 | Hata |
| 5,032,399 A | 7/1991 | Gorbach et al. |
| 5,705,160 A | 1/1998 | Bruce et al. |
| 5,709,857 A | 1/1998 | Morelli et al. |
| 5,965,128 A | 10/1999 | Doyle et al. |
| 6,060,050 A | 5/2000 | Brown et al. |
| 6,274,564 B1 | 8/2001 | Sarill et al. |

FOREIGN PATENT DOCUMENTS

| | | |
|---|---|---|
| DE | 2421066 | 3/1976 |
| EP | 0271364 | 12/1987 |
| WO | WO 9301823 | 2/1993 |
| WO | WO 9855131 A1 | 12/1998 |

OTHER PUBLICATIONS

Tuomola et al; The Effect of Probiotic Bacteria on the Adhesion of Pathogens to Human Intestinal Mucus; Fems Immunology and Medical Microbiology, Elsevier Science B.V., Amsterdam, NL, vol. 26, 1999, pp. 137–142.

Tuomola et al.; Adhesion of Some Probiotic and Dairy Lactobacillus Strains to Caco–2 Cell Cultures; Int'l. J. of Food Microbiology; 41 (1998); pp 45–51.

Salminen et al.; clinical Uses of Probiotics for Stabilizing the Gut Mucosal Barrier: Successful Strains and Future Challenges; Antonie Van Leeuwenhoek, Dordrecht, NL, vol. 70, No. 2/4, 1996; pp 347–358.

Greene et al.; Factors Involved in Adherence of Lactobacilli to Human Caco–2 Cells; Applied and Environmental Microbiology, vol. 60, No. 12; Dec. 1994; pp. 4487–4494.

Ouwehand et al; Adhesion of Inactivated Probiotic Strains to Intestinal Mucus; Letters in Applied Microbiology; vol. 31, No. 1, Jun. 2000; pp 82–86.

*Primary Examiner*—David M. Naff
*Assistant Examiner*—Deborah K. Ware
(74) *Attorney, Agent, or Firm*—Preston Gates & Ellis LLP; Louis C. Cullman

(57) ABSTRACT

Probiotic compositions are provided that comprise *Lactobacillus casei* strain KE01 having ATCC accession number PTA-3945. The disclosed probiotic compositions are useful in inhibiting enteric pathogen diseases in animals and in maintaining animal health. Methods of making and using *Lactobacillus casei* strain KE01 probiotic compositions are also disclosed as are methods of using these probiotic compositions.

33 Claims, 6 Drawing Sheets

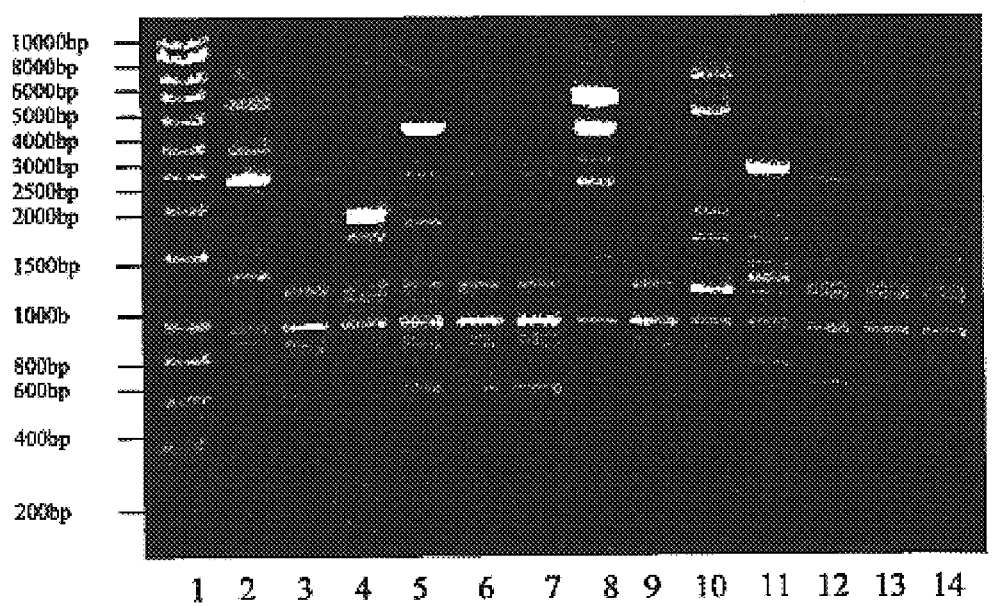

Figure 1. Lane 1: Molecular weight Marker HyperLadder I, Lane 2: strain KE-01, Lane 3: Lactobacillus acidophilus ATCC# 4356, Lane 4: Lactobacillus amylovorus ATCC# 33620, Lane 5: Lactobacillus brevis ATCC# 14869, Lane 6: Lactobacillus delbrueckii subsp. lactis ATCC# 12315, Lane 7: Lactobacillus fermentum ATCC# 14931, Lane 8: Lactobacillus helveticus ATCC# 15009, Lane 9: Lactobacillus paracasei subsp. paracasei ATCC# 25302, Lane 10: Lactobacillus plantarum ATCC# 14917, Lane 11: Lactobacillus casei ssp. rhamnosus ATCC#7469, Lane 12: Lactobacillus pentosus ATCC# 8041, Lane 13: Lactobacillus casei ssp. casei ATCC# 393, Lane 14: Lactobacillus reuteri ATCC#23272.

Attachment of KE01 could be visualized on bovine intestinal epithelia

KE01 colonized and formed biofilm on bovine intestinal epithelial mucosa

PROBIOTIC COMPOSITION CONTAINING LACTOBACILLUS CASEI STRAIN ATCC PTA-3945

RELATED APPLICATION

The present application claims priority to U.S. provisional patent application No. 60/256,528 filed Dec. 18, 2000, now abandoned, the entire contents of which are incorporated herein by reference.

FIELD OF THE INVENTION

The present invention discloses probiotic *Lactobacillus casei* preparations. Specifically, anti-infective, anti-diarrhea preparations derived from a newly characterized strain of *Lactobacillus casei* designated KE01 are disclosed. Related methods for preparing the probiotic compounds using *Lactobacillus casei* strain KE01 and related methods for using the KE01 probiotic compositions are also disclosed.

BACKGROUND OF THE INVENTION

The newly recognized probiotic *Lactobacillus casei* strain described herein has been designated KE01. Previously, this same organism had been designated *Lactobacillus casei* KE99 (see for example U.S. provisional application No. 60/256,528 and A. S. Naidu, X. Xie, D. A. Leumer, S. Harrison, M. J. Burrill and E. A. Fonda. 2001. Reduction of Sulfide, Ammonia Compounds and Adhesion Properties of *Lactobacillus casei* strain KE99 In Vitro. Curr. Microbiol. 43: In press.)

Lactic acid bacteria (LAB) are indigenous microflora of mammalian gastrointestinal tract that play an important role in the host microecology and have been credited with an impressive list of therapeutic and prophylactic properties. These therapeutic and prophylactic properties include, but not limited to the maintenance of microbial ecology of the gut, physiological, immuno-modulatory and antimicrobial effects. Other LAB associated attributes include enzyme release into the intestinal lumen that act synergistically with LAB adhesion to alleviate symptoms of intestinal malabsorption. Furthermore, the LAB enzymes help regulate intestinal pH which results in increased aromatic amino acid degradation. [Fuller, R. Probiotic foods—current use and future developments. IFI NR 3:23–26 (1993); Mitsuoka, T. Taxonomy and ecology of Bifidobacteria. Bifidobacteria Microflora 3:11 (1984); Gibson, G. R. et al., Probiotics and intestinal infections, p.10–39. In R. Fuller (ed.), Probiotics 2: Applications and practical aspects. Chapman and Hall, London, U.K. (1997); Naidu A S, et al., Probiotic spectra of lactic acid bacteria (LAB). Crit Rev Food Sci Nutr 39:3–126 (1999); Naidu, A. S., Clemens, R. A. Probiotics, p.431–462. In A. S. Naidu (ed.), Natural Food Antimicrobial Systems. CRC Press, Boca Raton, Fla. (2000)]

Lactic acid bacteria have also demonstrated the ability to significantly reduce sulfide and ammonia containing compounds in animal fecal waste and thus reduce the odor and toxicity associated with animal excrements. This ex vivo LAB application is becoming increasingly more important as agro-businesses expand and as communities continue their seemingly never ending encroachment into previously unoccupied rural areas. For example, LAB has been demonstrated to eliminate offensive odors and reduce hydrogen sulfide production associated with hatchery waste when cockerel chicks and shell waste are blended with a mixture containing 15% carbohydrate and LAB. Moreover, LAB compositions have demonstrated efficacy in diminishing the *Escherichia coli* and Salmonella content of hatchery waste to negligible levels. Additionally, the odor and viscosity of poultry offals such as broiler-processing waste is significantly reduced by *L. acidophilus* mediated lactic acid fermentation. Furthermore, preparations containing LAB have been reported to accelerate the breakdown of hard-to-degrade carbohydrates and decrease the ammonia production by porcine cecal bacteria. Finally, ex vivo *L. casei* FG1 and *L. plantarum* FG10 silage fermentation significantly reduces ammonia levels by inhibiting urea-splitting organisms. [Deshmukh, A. C., Patterson, P. H. Preservation of hatchery wastes by lactic acid fermentation. 1. Laboratory scale fermentation. Poult Sci 76:1212–1219 (1997); Russell, S. M. et al., Lactic acid fermentation of broiler processing waste: physical properties and chemical analyses. Poult Sci 71:765–770 (1992); Tibbetts, G. W. et al., Poultry offal ensiled with *Lactobacillus acidophilus* for growing and finishing swine diets. J Anim Sci 64:182–190 (1987); Sakata, T. et al., Probiotic preparations dose-dependently increase net production rates of organic acids and decrease that of ammonia by pig cecal bacteria in batch culture. Dig Dis Sci 44:1485–1493 (1999); Cai, Y. et al., Effect of applying lactic acid bacteria isolated from forage crops on fermentation characteristics, aerobic deterioration of silage. J Dairy Sci 82:520–526 (1999); Modler, H. W. et al., Bifidobacteria and bifidogenic factors. Can Inst Food Sci Tech 23:29–41 (1990)].

However, the greatest potential for LAB to improve life quality for man and domestic animals lies in LAB in vivo probiotic applications. In order for LAB to exhibit beneficial probiotic effects in vivo, the organisms must survive for extended time periods in the gastrointestinal tract. Therefore, it is critical that probiotic LAB strains be selected that possess qualities that prevent their rapid removal by gut contraction. Effective probiotic bacteria must able to survive gastric conditions and colonize the intestine, at least temporarily, by adhering to the intestinal epithelium. Consequently, LAB that demonstrate an enhanced ability to adhere to mucosal surfaces, and therefore possess improved bacterial maintenance and prolonged gastrointestinal tract residence times, have a competitive advantage over LAB that do not. [Salminen, S. et al., Clinical uses of probiotics for stabilizing the gut mucosal barrier: successful strains and future challenges. Antonie Van Leeuwenhoek 70:347–358 (1996); Conway, P. Selection criteria for probiotic microorganisms. Asia Pacific J Clin Nutr 5:10–14 (1996); Havenaar, R. et al., Selection of strains for probiotic use, p.209–224. In R. Fuller (ed.), Probiotics, the scientific basis. Chapman and Hall, London, U.K. (1992)].

Lactobacillus can successfully colonize the mammalian gastrointestinal tract through a number of different mechanisms. For example, some bacterial species bind to various sub-epithelial matrix proteins and specific receptors on the intestinal mucosa. Other species may adhere to mammalian intestinal cells via mechanisms that involve different combinations of carbohydrate and protein factors on the bacteria and host eucaryotic cell surfaces. However, regardless of the mechanism(s) of attachment, it is the ability of LAB to successfully colonize the human gastrointestinal tract that provides LAB with probiotic qualities. [Greene, J. D., Klaenhammer, T. R. Factors involved in adherence of lactobacilli to human Caco-2 cells. Appl Environ Microbiol 60:4487–4494 (1994); Sarem, F. et al., Comparison of the adherence of three Lactobacillus strains to Caco-2 and Int-407 human intestinal cell lines. Lett Appl Microbiol 22:439–442 (1996); Naidu, A. S., et al., Particle agglutination assays for rapid detection of fibronectin, fibriogen, and collagen receptors on *Staphylococcus aureus*. J Clin Microbiol 26:1549–1554 (1988); Wadstrom, T. et al., Surface properties of lactobacilli isolated from the small intestines of pigs. J Appl Bacteriol 62:513–520 (1987); Bernet, M. F. et al., *Lactobacillus acidophilus* LA 1 binds to cultured human intestinal cell lines and inhibits cell attachment, invasion by entero-virulent bacteria. Gut 35:483–489 (1994); Jin, L. Z. et al., Effect of adherent Lactobacillus spp. on in vitro adherence of salmonellae to the intestinal epithelial cells of chicken. J Appl Bacteriol 81:201–206 (1996); Reid, G. et al., Influence of lactobacilli on the adhesion of *Staphylococcus aureus* and *Candida albicans* to fibers and epithelial cells. J Ind Microbiol 15:248–253 (1995)].

Generally speaking probiotic bacteria exert their beneficial effects by displacing invasive or toxigenic pathogenic enteric bacteria (enteric pathogens) from the intestinal mucosa through a competitive binding process. Enteric pathogens such as, but not limited to enteropathogenic *Escherichia coli* (EPEC), enterotoxigeneic *E. coli* (ETEC), *Salmonella enteriditis, Yersina pseudotuberculosis* and *Listeria monocytogenes* must be able to successively colonize an animal's intestinal tract in order to cause disease.

The mechanisms these organisms use to effectively colonize the intestine are varied. For example, ETEC bearing CFA/I or CFA/II adhesive factors specifically adhere to the brush border of the polarized epithelial human intestinal Caco-2 cells in culture. *S. typhimurium* and EPEC adhere to the brush border of differentiated human intestinal epithelial Caco-2 cells in culture, whereas *Y. pseudotuberculosis* and *L. monocytogenes* bind to the periphery of undifferentiated Caco-2 cells.

Recently, heat-killed *L. acidophilus* preparations have been proven to be effective probiotic compositions. Heat-killed *L. acidophilus* preparations have been shown to displace known enteric pathogens from the lining of a test animal's intestinal wall in a dose dependent manner. Consequently, enteric pathogens were unable to colonize the animal's gastrointestinal tract thus preventing disease. For example, *L. acidophilus* (Lacteol® strain) was found to inhibit this adhesion in a dose-dependent manner of *E. coli* strain B41 (ECB41). In other experiments live and heat-killed *L. acidophilus* strain LB successfully inhibited both Caco-2 cell association and invasion of enteric pathogens. An in yet another study, heat-killed *L. acidophilus* strain LB was shown to completely inhibit ETEC adhesion to Caco-2 cells. [Fourniat, J. et al., Heat-killed *Lactobacillus acidophilus* inhibits adhesion of *Escherichia coli* B41 to HeLa cells. Ann Rech Vet 23:361–370 (1992); Chauviere, G. et al., Competitive exclusion of diarrheagenic *Escherichia coli* (ETEC) from human enterocyte-like Caco-2 cells by heat-killed Lactobacillus. FEMS Microbiol Lett 70:213–217 (1992)]. Coconnier, M. H. et al., Inhibition of adhesion of enteroinvasive pathogens to human intestinal Caco-2 cells by *Lactobacillus acidophilus* strain LB decreases bacterial invasion. FEMS Microbiol Lett 110:299–305 (1993)].

As previously explained, probiotic compositions are generally defined as microbial dietary supplements that beneficially affect the host by improving intestinal microbial balance. The two major genera of microorganisms commonly associated with probiotics include Lactobacillus sp and Bifidobacteria sp. The beneficial effects attributed to probiotics include increased resistance to infectious diseases, healthier immune systems, reduction in irritable bowel syndrome, reductions in blood pressure, reduced serum cholesterol, milder allergies and tumor regression. However, in spite of recent scientific advances and the publication of limited in vivo and in vitro experimental evidence supporting the efficacy of probiotic compositions, the major studies reporting these and other benefits have relied on antidotal evidence.

Examples of publications depending on antidotal and limited in vitro data include U.S. Pat. Nos. 3,957,974, 4,210,672, 4,314,995, 4,345,032, 4,579,734, 4,871,539, 4,879,238 and 5,292,362 (the "Hata" patents). The Hata patents disclose various subspecies of Lactobacillus spp and report beneficial probiotic-like effects. However, the Hata patents do not disclose or describe a Lactobacillus species that demonstrates avid binding to sub-epithelial matrices and competitive exclusion and microbial interference with bacterial enteric pathogens.

U.S. Pat. No. 6,060,050 (the "'050 patent") discloses a preparation consisting of probiotic microorganisms dispensed in a starch containing medium used to protect the organism during storage, serves to transport the organism to the large bowel and provides a growth promoting substrate. However, the '050 patent does not provided data that directly demonstrates probiotic activity against enteric pathogens.

U.S. Pat. No. 5,965,128 (the "'128 patent") discloses the treatment of enteric diseases caused by *E. coli* O157:H7 (enterohemorrhagic *E. coli*). However, the probiotic compositions of the '128 patent only includes non-pathogenic strains of *E. coli*, no Lactobacillus sp are disclosed. Consequently, while the non-pathogen enteric organisms of the '128 patent may afford the recipient "probiotic-like" protection against enterohemorrhagic *E. coli*, other beneficial qualities associated with Lactobacillus sp and Bifidobacteria sp are absent.

U.S. Pat. Nos. 4,839,281, 5,032,399 and 5,709,857 (the "'857 patent") discloses several strains of *Lactobacillus acidophilus* that adhere to intestinal mucosal cells. Moreover, the '857 patent discloses a *Lactobacillus acidophilus* strain that inhibits the growth of certain enteric pathogens. However, the '857 patent does not disclose *L. casei* strains having the proven beneficial qualities associated with the *L. acidophilus* cultures of the '857 patent.

Therefore, there remains a need for new strains of Lactobacillus sp. that exhibit probiotic activities. Particularly, there is a need for more strains of Lactobacillus sp. that have the proven capacity to reduce enteric pathogen diseases and increase animal vitality and health.

SUMMARY OF THE INVENTION

It is an object of the present invention to provide a new strain of Lactobacillus sp that has demonstrated probiotic properties.

It is another object of the present invention to provide a new strain of Lactobacillus spp that has anti-enteric pathogen probiotic activity.

It is yet another object of the present invention to provide a new strain of Lactobacillus sp. that maintain animal health and vitality.

It is still another object of the present invention to provide dietary supplements and pharmaceutical preparations made from Lactobacillus sp. having demonstrated probiotic properties.

The present invention fulfills these and other objects by providing a new strain of *Lactobacillus casei* designated KE01 that possesses scientifically proven probiotic properties including demonstrated in vivo anti-enteric pathogen activity. Moreover, the present invention provides dietary supplements and pharmaceutical preparations composed of L. casei strain KE01 that are formulated in a sugar complex composed of trehalose and fructooligosaccharides that provides long term protection to the organism and helps maintain its proven probiotic properties.

There is a need for new probiotic formulations that can be used to treat and prevent enteric-pathogen infections and help maintain the health and vitality of humans and livestock. Recently, the Federal Food and Drug Administration (FDA) has intensified its campaign against the over prescription and clinical abuse of antibiotics. The excessive use of antibiotics has increased in the number of human and animal pathogens that are resistant to first-line antibiotics resulting in an increase in infections that do not respond to conventional antimicrobial therapies. Moreover, the prophylactic use of antibiotics in animal feed has resulted in an alarming increase in livestock intestinal infections resulting in diminished herd size and animal weight due to nutrient malabsorption. Consequently, the number of healthy animals suitable for human consumption has dropped, and those that do survive long enough to reach market have significantly lower weights and consequently reduced meat quality.

One means of preventing the rapid spread of drug resistant enteric pathogens in humans and livestock is to significantly reduce antibiotic use. However, the spread of communicable diseases including enteric infections is inevitable due to over crowding of farms and cities. Consequently, before prophylactic antibiotic use can be completely discontinued a suitable antimicrobial alternative must be available. Recent studies have indicated that the use of foodstuffs and dietary supplements containing specific strains of probiotic microorganisms can help prevent, and in many cases actually cure, enteric pathogen diseases. However, many of the probiotic formulas currently marketed rely on organisms including Lactobacillus spp and Bifidobacteria sp (and other genera) that have not been subjected to scientific scrutiny using approved methods for assessing probiotic efficacy. Consequently, too many of the "probiotic" formulas currently available lack proven in vivo anti-enteric pathogen activity. Moreover, many of the clinically effective probiotic formulations commercially available are not stable upon storage and therefore do not deliver effective amounts of viable probiotic bacteria to the user. The present inventor has tested many commercially available preparations and found microbial viability well below stated concentrations and in many cases the present inventor has found that these commercial preparations did not contain any viable bacteria.

The present inventor has developed methods for preparing and packaging a new strain of L. casei, designated KE01. This new strain of L. casei was originally from a traditional fermented yoghurt-like Asian dairy product by the present inventor. Subsequently, the present inventor characterized the isolate and the strain deposited with the American Type Culture Collection (ATCC, MD, USA)). Lactobacillus casei strain KE01 has been given the ATCC depository number PTA-3945. Moreover, the present inventor has developed preparations that maintain L. casei KE01 viability such that a clinically effective dose of viable probiotic microorganisms reaches the host.

The present invention provides a L. casei strain (KE01) that interferes with bacterial adherence (microbial interference) of enteric pathogens such as, but not limited to enteropathogenic and enterotoxigenic E. coli, Helicobacter pylori, Campylobacter jejuni, S. typhimurium, and S. enteritidis to a variety of mammalian cell types. Moreover, the Lactobacillus of the present invention can also competitively exclude (competitive exclusion) these, and other bacterial pathogens, from binding to many mammalian cells. The beneficial properties associated with the novel Lactobacillus strain of the present invention have resulted in improved probiotic dietary supplements that support general human and animal health. Moreover, the present invention can be used to provide prophylactics, therapeutics and palliatives (collectively referred to herein as "probiotics") for conditions such as, but not limited to, traveler's diarrhea, gastrointestinal infections, hemolytic uremic syndrome, and gastric ulcers.

Additional novel features and qualities of this new L. casei strain KE01 include, but are not limited to, L. casei KE01's ability to reduce sulfide concentrations by a factor exceeding 300 ppm within 48 hours when exposed to a growth medium containing approximately 2000 ppm of sulfides and the demonstration of avid binding to sub-epithelial matrices including Bio-coat™ (Collagen type-I, Collagen type IV, laminin, and fibronectin), Matrigel™ and Caco-2 cell monolayer. Most importantly, a reconstituted, freeze-dried preparation of the L. casei of the present invention has been shown to effectively detach collagen-adherent E. coli.

The methods used to maintain the viability of the L. casei of the present invention and preserve its E. coli displacement qualities include, but are not limited the use of the sugar trehalose and moisture and packaging the final compositions in oxygen proof polymer-lined (e.g. Mylar®) foil pouches.

These and other beneficial probiotic properties of the new strain of Lactobacillus will be further evident by the following, non-limiting, detailed description of the present invention.

BRIEF DESCRIPTION OF THE FIGURES

FIG. 1 depicts the genomic fingerprint of Lactobacillus casei strain KE01 on 1% agarose gel compared to 12 different Lactobacillus type strains based on Randomly Amplified Polymorphic DNA (RAPD) assay.

DETAILED DESCRIPTION OF THE INVENTION

Figure 2:
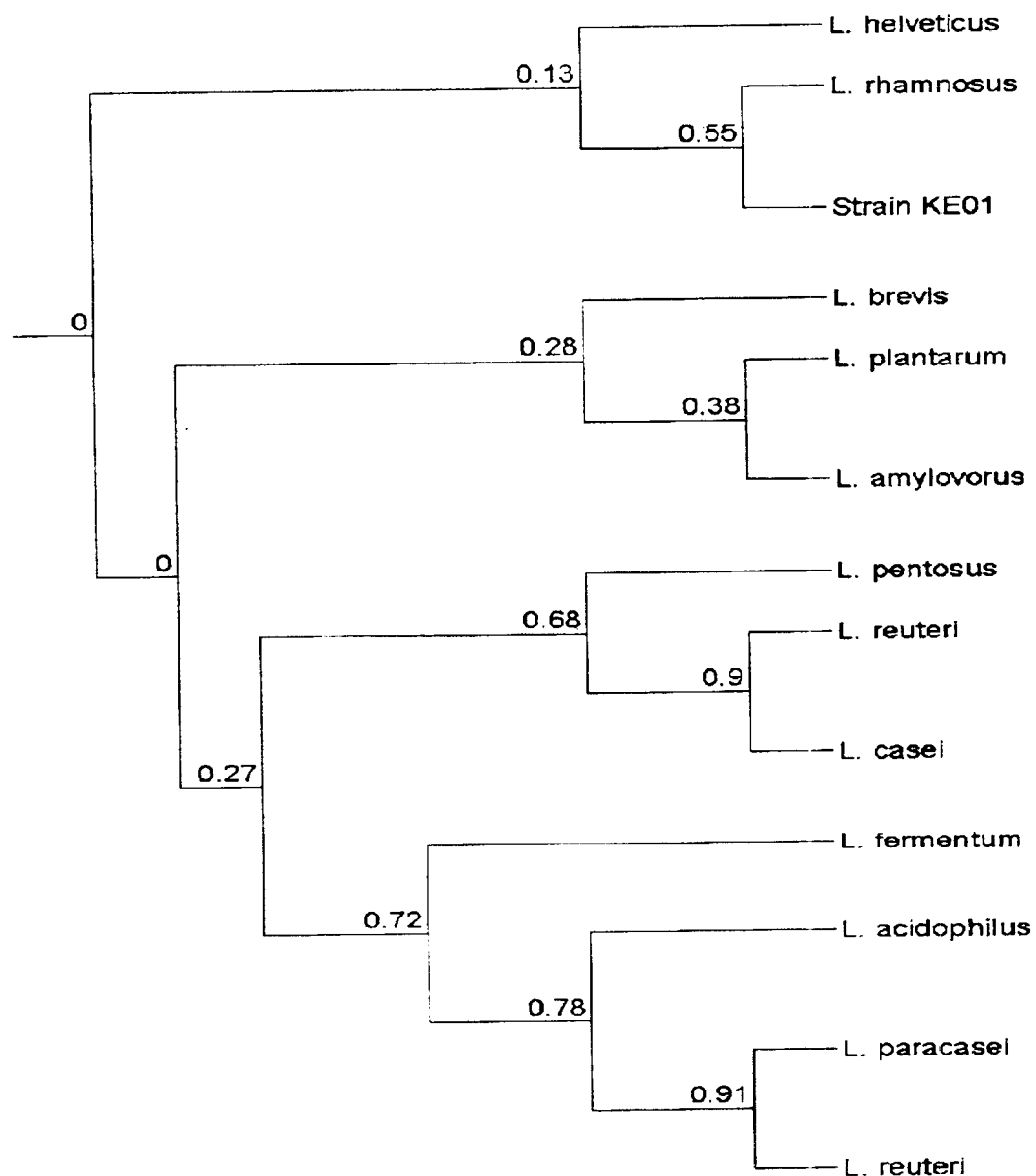
FIG. 2 depicts the phylogenic dendogram deduced from genomic fingerprinting and the relatedness of Lactobacillus strain KE01 with other species of Lactobacillus type strains.

One embodiment of the present invention is a dietary supplement comprising approximately from $10^5$ to $10^{11}$ colony forming units of viable lactobacilli per gram. In another embodiment of the present invention the dietary supplement comprises from approximate $10^5$ to $10^{11}$ non-viable lactobacilli per gram. The lactobacillus of the present invention is *Lactobacillus casei* strain KE01 having the American Type Culture Collection (ATCC) accession number PTA-3945. A colony forming unit (CFU) of *Lactobacillus casei* KE01 equates to one bacterial cell. Although generally only used when referring to viable bacteria, the term colony forming unit, or CFU will also be defined as a single non-viable bacterial cell when referring to embodiments of the present invention composed of non-viable lactobacilli compositions.

In one embodiment of the present invention the dietary supplement comprises a gelatin capsule filled with a dried lactobacillus composition. In another embodiment the dietary supplements is in the form of a liquid preparation. In yet another embodiment of the present invention the dietary supplement is in the form of an anal or vaginal suppository. When used as a suppository it may be formed into a convenient bolus and may contain non-toxic lubricants, stabilizers, waxes and the like to ease in the administration. In another embodiment of the present invention the lactobacillus dietary supplement may be compounded with foods such as, but not limited to dairy products, grains, breads, meats, fruits, vegetables, rice and the like. The form the lactobacillus dietary supplement of the present invention assumes is not important and is non-limiting.

Throughout this specification the present invention may be referred to as a probiotic composition, a lactobacillus containing composition, a dietary supplement, a freeze-dried powder or lactobacillus composition. All of these aforementioned terms mean a composition, regardless of form or the presence or absence of other ingredients, that contains viable or non-viable *Lactobacillus casei* strain KE01 having ATCC accession number PTA-3945 or its genetic equivalent as determined using the methods detailed herein.

In one embodiment of the present invention the lactobacilli composition is freeze dried using standard methods known to those having ordinary skill in the art of food science. In another embodiment the lactobacilli composition of the present invention the lactobacilli composition is air-dried. In yet another embodiment the lactobacilli composition is a paste. In still another embodiment the lactobacilli composition of the present invention is a liquid.

The lactobacilli compositions of the present invention may or may not be compounded with additional ingredients. For example, in one embodiment of the present invention the lactobacilli composition is mixed with a carbohydrate selected from the group consisting of trehalose, glucose, sucrose, fructose, maltose and combinations thereof. The carbohydrate(s) may comprise from approximately 50% to 98% of the entire composition. In another embodiment proteins such as albumin and/or whey may or may not be added to the lactobaclili compositions of the present invention.

The lactobacilli compositions of the present invention may be taken orally as a bolus in the form of a gelatin capsule, pressed tablet, or gel cap. In another embodiment the lactobacilli compositions of the present invention may be taken orally in the form of a liquid beverage. The liquid beverage may contain other ingredients such as, but not limited to flavor enhancers, sweeteners, viscosity enhancers and other food additives. The present invention may also be taken together with other foods either separately or compounded therewith.

In one embodiment of the present invention an animal is provided with a single dose containing from approximately $10^5$ to $10^{11}$ lactobacilli per gram of probiotic composition. The total amount consumed will depend on the individual needs of the animal and the weight and size of the animal. The preferred dosage for any given application can be easily determined by titration. Titration is accomplished by preparing a series of standard weight doses each containing from approximately $10^5$ to $10^{11}$ lactobacilli per gram. A series of doses are administered beginning at 0.5 grams and continuing up to a logical endpoint determined by the size of the animal and the dose form. The appropriate dose is reached when the minimal amount of lactobacilli composition required to achieve the desired results is administered. The appropriate dose is also known to those skilled in the art as an "effective amount" of the probiotic compositions of the present invention.

For example, if it is desired to reduce the symptoms associated with irritable bowel syndrome in an animal, one measured dose as described above is administered daily, escalating the dose each successive day in 0.5 grams increments until symptoms subside. In one embodiment of the present invention the preferred dose is between approximately $10^3$ to $10^8$ viable lactobacilli per kilogram of body weight (the weight of animal recipient) per day. This equates to approximately 10 billion viable *Lactobacillus casei* strain KE01 per day for the average healthy adult human. By extrapolation, it is a simple matter to calculate the approximate dose appropriate for any animal of any weight. It is understood that this is a non-limiting example that can be varied as appropriate by persons having skill in the art of prescribing probiotic compositions or by using the titration method provided above.

The probiotic compositions of the present invention can be administered to any animal in need of thereof including, but not limited to mammals, birds, reptiles and fish. Typical applications include administering the probiotic compositions of the present invention to humans, horses, swine (pigs), cows, sheep, dogs, cats, rabbits, chickens, turkeys, pheasants, quail, parakeets, parrots, and other wild and domesticated animals.

Specifically, the probiotic compositions of the present invention can be used to inhibit or treat enteric pathogen-associated diseases when administered to an animal in need thereof using the methods described in the present specification. Enteric pathogen diseases include those diseases caused by pathogens such as diarrhea, irritable bowel syndrome and intestinal hemorrhages. Examples of enteric pathogens associated with these diseases include, but not limited to enteropathogenic *Escherichia coli* (EPEC), enterotoxigeneic *E. coli* (ETEC), *Salmonella enteriditis, Yersina pseudotuberculosis* and *Listeria monocytogenes*. It is theorized by the present inventor, and not offered as a limitation, that the inhibition and treatment of the enteric pathogen diseases is accomplished by the probiotic composition of the present invention through a competitive binding process. That is, the probiotic lactobacilli of the present invention compete with enteric pathogens for binding sites on the intestinal mucosa. Because the probiotic lactobacilli of the present invention have a higher affinity and avidity for these binding sites than the enteric pathogens, the probiotic lactobacilli of the present invention displace the enteric pathogens into the intestinal milieu where they are harmlessly flushed from the intestines by normal metabolic processes. In vivo examples of this above described competitive binding and its efficacy in inhibiting and treating enteric pathogen diseases is provided in detailed examples below and in the accompanying figures.

The following technical discussion provides detailed teachings. In Section I one of ordinary skill in the art is taught how to isolate and identify probiotic lactobacilli, specifically, the probiotic Lactobacillus of the present invention, *Lactobacillus casei* strain KE01. In Section II specific examples are provided that teach how to prepare the probiotic compositions of the present invention and the testing that was conducted to scientifically validate the probiotic qualities demonstrated by the probiotic compositions of the present invention. It is understood that these detailed examples are not intended as limitations.

I. Isolation and Characterization of *Lactobacillus casei* Strain KE01

A. Isolation of Candidate Probiotic Bacteria

The probiotic organism of the present invention was isolated from a traditional fermented yogurt-like Asian dairy product. The screening process was limited to traditional fermented yogurt-like Asian dairy products with at least a ten-year history of safe human consumption. Probiotic bacteria isolation was performed using three selective microbiological media using methods known to those of ordinary skill in the art of microbiology. Lactobacilli selective media included SL medium supplemented with 0.05% cystein, Bifidobacterium spp. were selected for using trypticase phytone yeast extract medium containing antibiotics; and for Streptococcus spp. were isolated using trypticase yeast extract cystein medium.

Candidate probiotic lactobacilli were be catalase negative, glucose homo-fermentative, Gram-positive non-spore forming rods demonstrating low pH, gastric acid and bile resistance. The lactobacilli isolates' inability to grow at pH 9.0 coupled with their ability to grow on acetate containing media served to distinguish them from Carnobacterium spp. A total of 81 isolates were classified as candidate probiotic lactobacilli based on these criteria and were further characterized with respect to the following criteria: i) resistance to low pancreatic juice; ii) adherence ability to sub-epithelial collagen matrices; and iv) their capacity to reduce ammonia and sulfide containing compounds.

After analyzing all 81-candidate probiotic lactobacilli, two strains were identified having all of the above-identified characteristics. These strains were designated strain KE97 and strain KE99 (re-designated KE01). Finally the growth-multiplication rate (generation time as determined by impedance detection using BioMerieux™ Bactometer System), stability of strains in continuous culture, freeze-drying and revival characteristics, and aroma/flavor profiles were ascertained for each strain.

The isolated *Lactobacillus casei* strain KE01 organism is maintained in a biologically pure culture for use in preparing probiotic compositions of the present invention. As used herein biologically pure culture refers to a bacteriological culture that results in only one identifiable organism when cultured on solid or semi-solid microbiological culture media. It is understood that extremely low levels of cells from other bacterial species may be present; however, these cells are either non-viable, non-cultivable or below the threshold of detection using classical, non-genome-based, microbiological techniques. The term "non-genome-based" is intended to excluded such methods as PCR detection or similar methods used to detect microbial DNA or RNA.

Moreover, it is understood that whenever the *Lactobacillus casei* strain KE01 (or may be referred to as simply KE01) powders, pastes, gels, bolus or other probiotic compositions are made in accordance with the teachings of the present invention are described herein, that the *Lactobacillus casei* strain KE01 was derived from a biologically pure culture.

B. DNA Fingerprinting by Random Amplified Polymorphic DNA (RAPD) Assay.

The RAPD protocol uses PCR for generating a unique fingerprint for bacterial identification. The analysis by PCR can be performed in a rapid and reliable manner. Accordingly, the RAPD assay has been used for molecular identification and finger printing of strain KE01. A total of 12 Lactobacillus spp. type strains from the ATCC collection were finger printed and compared with the KE01. For the DNA fingerprinting all the lactobacillus strains were cultivated overnight in MRS broth (Difco). The Lactobacillus strains analyzed for DNA fingerprint are listed in Table 1.

TABLE 1

| Lactobacillus spp. | SOURCE |
| --- | --- |
| Lactobacillus strain KE01 | en-N-tech, Inc., California, USA |
| *Lactobacillus acidophilus* ATCC 4356 | Human [L 917; IFO 13951; NCIB 8690] |
| *Lactobacillus amylovorus* ATCC 33620 | Cattle waste-corn silage |
| *Lactobacillus brevis* ATCC 14869 | Human feces |
| *Lactobacillus casei* subsp. *casei* ATCC 393 | Cheese [IAM 12473; Orland L-323] |
| *Lactobacillus casei* subsp. *rhamnosus* ATCC 7469 | [BUCSAV 227; P. A. Hansen 300; NCDO 243; NCIB 6375; NCTC 6375; NRC 488] |
| *Lactobacillus delbrueckii* subsp. *lactis* ATCC 12315 | Swiss cheese [DSM 20072; IAM 12476; NCDO 1438] |
| *Lactobacillus fermentum* ATCC 14931 | Fermented beets [NCIB 11840] |
| *Lactobacillus helvaticus* ATCC 15009 | Swiss cheese |
| *Lactobacillus paracasei* subsp. *paracasei* ATCC 25302 | [NCDO 151; R094] |
| *Lactobacillus pentosus* ATCC 8041 | [DSM 20314; NCDO 363; NCIB 8026] |
| *Lactobacillus plantarum* ATCC 14917 | Pickled cabbage [IAM 124771] |
| *Lactobacillus reuteri* ATCC 23272 | Human feces | matrices such as Biocoat™ Matrigel (Becton Dickinson, Bedford, Mass.) and to cultured intestinal epithelial cells (Caco-2 cell line); iii) their ability to competitively exclude enterohemorrhagic *E. coli* serotype O157:H7 adherent to DNA Extraction Method DNA was extracted from the lactobacilli using the Wizard Genomic DNA Purification Kit (Promega, Wis., USA). Briefly, 1 mL of 24-h grown MRS broth culture of each lactobacillus spp. was harvested by centrifugation, cells were resuspended in 50 mM EDTA and treated with 10 mg/mL lysozyme (Sigma, MO, USA) at 37° C. for 60 min. Lactobacilli cells were pelleted by centrifugation and supernatant was removed. The bacterial pellets were resuspended in the nuclei lysis solution and incubated at 80° C. for 5 minutes. Cell suspension was allowed to cool to room temperature and RNAse was mixed into the solution. The suspension was incubated at 37° C. for 60 min. After incubation, protein precipitation solution was added to the mixture. Solution was mixed on vortex and incubated on ice for 5 min. The mixture was centrifuged for 3 min at 15K×g, supernatant was transferred to a fresh tube and the DNA was precipitated with isopropyl alcohol. The DNA was centrifuged and the isopropyl alcohol was aspirated. The DNA pellet was washed with 70% ethanol and harvested by centrifugation. Ethanol was removed and the pellet was allowed to dry. The DNA was resuspended in tris-EDTA buffer.

PCR Amplification of Extracted DNA

One microliter of the extracted DNA was used in the PCR reactions, which were carried out on the iCycler (Bio-Rad, CA, USA) using a single arbitrary nucleotide sequence according to Cocconcelli, et al. (1995). A 2× PCR solution-Premix Taq (Takara, Shiga, Japan) was used for each reaction. Each reaction contained a total volume of 50 µL, 1.25 units of Takara Ex Taq DNA Polymerase, 1× Buffer, 200 µM dNTP Mix (2.5 mM each). Final concentration of the primer was 4 µM, and the primer used for the amplification was 5'-AgCAgCgTgg-3' (Operon Technologies, Inc., CA, USA). The reaction mixtures with the template DNA were cycled through the following temperature profile: 1 cycle of 94° C. for 5 min; 40 cycles of 94° C. for 1 min; 29° C. for 1 min; ramp to 72° C. 1.5 min and held at 72° C. for 1.5 min; 1 cycle of 72° C. for 2 min; and held at 4° C. [Cocconcelli, PS et al., Development of RAPD protocol for typing of strains of lactic acid bacteria and entercocci. Lett. Appl. Microbiol. 21:376–379 (1995)].

Gel electrophoresis

Aliquots of each RAPD amplified reaction (10 µL) were analyzed by 1% (wt/vol) agarose gel electrophoresis in Tris-borate-EDTA buffer according to Sambrook et al. (1989). Gels were run for 2 hr at 120V without cooling. The DNA molecular weight marker Hyperladder I (Bioline, Randolph, Mass., USA) was used as the standard. After electrophoresis the gel was stained with ethidium bromide (5 µg/mL) for 10 min, washed for 5 min and visualized and analysed on a Fluor-S MultiImager (BioRad, CA, USA). [Sambrook, J., Fritsch, E. F., Maniatis, T. Molecular Cloning—A Laboratory Manual, $2^{nd}$ Edition. Cold Spring Harbor Laboratory Press, New York (1989)].

The RAPD assay using a single 10-mer primer produced distinct banding patterns of variable intensities and numbers of amplified products on 1% agarose gel with DNA samples of various lactobacillus reference strains and strain KE01. Comparison of the different species fragments on the gel to the reference Lactobacillus spp. was noted. The banding pattern with documentation as depicted in FIG. 1 and TABLE 2 serves to uniquely identify strain KE01 and provided a genomic fingerprinting library. Based on the genomic fingerprinting a dendogram was deduced as shown in FIG. 2. Ward's Cluster Method of Phylogenic Analysis was applied. This method minimizes the Sum of Squares of any two clusters that can be formed at each step, creating clusters of small sizes. Based on the phylogenic analysis, strain KE01 showed 13% homology with *Lactobacillus helvaticus* ATCC15009 and 55% homology with *Lactobacillus casei* ssp. *rhamnosus* ATCC7469.

A pure culture of *Lactobacillus casei* strain KE01 was deposited with the American Type Culture Collection, Bethesda, Md., which was assigned the number ATCC PTA-3945.

TABLE 2

| Lane Number | Band Number | Mol. Wt. (bp) | Identification |
|---|---|---|---|
| 2 | 1 | 4661.359 | Strain KE-01 |
| 2 | 2 | 2986.357 | |
| 2 | 3 | 2457.454 | |
| 2 | 4 | 2255.342 | |
| 2 | 5 | 1565.537 | |
| 2 | 6 | 1354.07 | |
| 2 | 7 | 991.287 | |
| 2 | 8 | 904.264 | |
| 2 | 9 | 596.721 | |
| 3 | 1 | 2457.454 | *Lactobacillus acidophilus* |
| 3 | 2 | 1231.998 | ATCC# 4356 |
| 3 | 3 | 1003.944 | |
| 3 | 4 | 904.264 | |
| 3 | 5 | 861.774 | |
| 3 | 6 | 617.813 | |
| 4 | 1 | 4721.177 | *Lactobacillus amylovorus* |
| 4 | 2 | 1969.14 | ATCC# 33620 |
| 4 | 3 | 1894.057 | |
| 4 | 4 | 1725.33 | |
| 4 | 5 | 1672.497 | |
| 4 | 6 | 1271.414 | |
| 4 | 7 | 1203.24 | |
| 4 | 8 | 1023.9 | |
| 5 | 1 | 3611.082 | *Lactobacillus brevis* |
| 5 | 2 | 3259.978 | ATCC# 14869 |
| 5 | 3 | 2534.42 | |
| 5 | 4 | 2087.693 | |
| 5 | 5 | 1864.831 | |
| 5 | 6 | 1271.414 | |
| 5 | 7 | 1031.994 | |
| 5 | 8 | 940.583 | |
| 5 | 9 | 888.576 | |
| 5 | 10 | 651.854 | |
| 6 | 1 | 2545.999 | *Lactobacillus delbrueckii* |
| 6 | 2 | 1281.464 | ssp. *lactis* ATCC# 12315 |
| 6 | 3 | 1036.064 | |
| 6 | 4 | 940.583 | |
| 6 | 5 | 892.472 | |
| 6 | 6 | 645.528 | |
| 7 | 1 | 7490.875 | *Lactobacillus fermentum* |
| 7 | 2 | 2545.999 | ATCC# 14931 |
| 7 | 3 | 1732.051 | |
| 7 | 4 | 1281.464 | |
| 7 | 5 | 1036.064 | |
| 7 | 6 | 953.011 | |
| 7 | 7 | 900.317 | |
| 7 | 8 | 655.041 | |
| 8 | 1 | 14117.898 | *Lactobacillus helveticus* |
| 8 | 2 | 4936.649 | ATCC# 15009 |
| 8 | 3 | 3634.241 | |
| 8 | 4 | 2776.318 | |
| 8 | 5 | 2394.989 | |
| 8 | 6 | 2105.687 | |
| 8 | 7 | 1529.442 | |
| 8 | 8 | 1036.064 | |
| 9 | 1 | 3588.07 | *Lactobacillus paracasei* |
| 9 | 2 | 1271.414 | ssp. *paracasei* ATCC# |
| 9 | 3 | 1107.771 | 25302 |
| 9 | 4 | 1027.939 | |
| 9 | 5 | 932.388 | |
| 9 | 6 | 892.472 | |
| 9 | 7 | 636.154 | |
| 10 | 1 | 6200.546 | *Lactobacillus plantarum* |
| 10 | 2 | 4968.224 | ATCC# 14917 |
| 10 | 3 | 4263.326 | |
| 10 | 4 | 1969.14 | |
| 10 | 5 | 1685.552 | |
| 10 | 6 | 1322.462 | |
| 10 | 7 | 1231.998 | |
| 10 | 8 | 1027.939 | |

TABLE 2-continued

| Lane Number | Band Number | Mol. Wt. (bp) | Identification |
|---|---|---|---|
| 10 | 9 | 223.284 | |
| 11 | 1 | 2592.843 | Lactobacillus casei ssp. rhamnosus ATCC# 7469 |
| 11 | 2 | 2324.117 | |
| 11 | 3 | 1685.552 | |
| 11 | 4 | 1430.79 | |
| 11 | 5 | 1312.091 | |
| 11 | 6 | 1212.751 | |
| 11 | 7 | 1011.88 | |
| 11 | 8 | 780.732 | |
| 12 | 1 | 9035.455 | Lactobacillus pentosus ATCC# 8041 |
| 12 | 2 | 6787.29 | |
| 12 | 3 | 2405.288 | |
| 12 | 4 | 2198.014 | |
| 12 | 5 | 1453.497 | |
| 12 | 6 | 1261.443 | |
| 12 | 7 | 1198.513 | |
| 12 | 8 | 982.651 | |
| 12 | 9 | 667.942 | |
| 13 | 1 | 2945.799 | Lactobacillus casei ssp. casei ATCC# 393 |
| 13 | 2 | 2374.522 | |
| 13 | 3 | 2169.899 | |
| 13 | 4 | 1436.433 | |
| 13 | 5 | 1217.534 | |
| 13 | 6 | 974.089 | |
| 13 | 7 | 876.989 | |
| 13 | 8 | 839.445 | |
| 13 | 9 | 661.46 | |
| 13 | 10 | 583.785 | |
| 14 | 1 | 2324.117 | Lactobacillus reuteri ATCC# 23272 |
| 14 | 2 | 2114.743 | |
| 14 | 3 | 1402.903 | |
| 14 | 4 | 1184.442 | |
| 14 | 5 | 944.708 | |
| 14 | 6 | 832.131 | |
| 14 | 7 | 639.264 | |

II. Examples of the Present Invention

Bulk Lactobacilli strain KE01 as used in the following Examples was mass-produced using standard fermentation processes as known to those having ordinary skill in the art of fermentation microbiology. The purified Lactobacillus strain KE01 was then used in the preparation of various delivery systems including fine powder, bolus capsule, gel, and dry animal feed-mixtures as follows:

EXAMPLE-1

Preparation of the Lactobacilli Strain KE01 Compositions of the Present Invention
Preparation of Freeze-Dried KE01 into a Fine Powder-Form A pure culture of Lactobacillus KE01 (starter) stored frozen at −22° C., was revived in a fermentation broth media containing proteins, vitamins, minerals and carbohydrate source. A seed culture was prepared in a fermentor attached to NBS 1500L fermentation vessel. Microbial purity was monitored at defined time points (through log phase and end cycle) during the fermentation process. The microbial mass was harvested in a sanitized separator and the slurry of cell concentrate was freeze-dried after mixing with carriers containing a mixture of anhydrous dextrose and trehalose. Spray-dried Grade-A low-heat non-fat pasteurized milk was used as a cryoprotectant. The freeze-dried KE01 concentrate was milled to fine powder using a sanitized milling equipment. The quality of KE01 powder was assured for purity and viability prior to use. Blending of KE01 powder into mixtures:

All operations are performed in a temperature (74–76° F.) and humidity (30–40%) controlled environment. KE01 powder (approximately $10^{11}$ CFU/g lactobacilli) and other ingredients listed in the composition below were introduced into a closed system for blending. Serial geometric dilution is done to ensure homogenous distribution of all components. Mixing is done in a mass flow bin tumbling system with customized geometry to ensure bed splitting and cross flow. Once mixed, the powders are maintained in the closed system until packaged into 5 lb pails. The blended powder is filled into suitable containers (pails, unit dose packs, etc.) with moisture absorbing packs or inherent vapor barrier properties, and sealed with an airtight lid.

It is understood to those having ordinary skill in the art that the term "approximately" is used to provide a reasonable element of error inherent in weighing and manufacturing bulk materials. As used herein "approximately" will include an error factor of from 0.1 to 0.5%. Furthermore, it is understood by those having ordinary skill in the art that the amount of materials used to formulate a final composition must total 100% and cannot exceed 100%. All percentages are on a weight percentage basis. For example, and not intended as a limitation, in one embodiment of the present invention the probiotic composition made in accordance with the teachings of the present invention comprise from approximately 1 to 5% of KE01 powder having from approximately $10^5$ to $10^{11}$ CFU of KE01 per g and from 95 to 99% inert or active ingredients selected from the group consisting of, but not limited to, carbohydrates, lipids, polypeptides, fatty acids, phytochemicals and combinations thereof.

Carbohydrates that may be used in accordance with the teachings of the present invention include monosaccharides, disaccharides, oligosaccharides and polysaccharides such as, but not limited to trehalose, maltose, sucrose, dextrose, lactose, inulin, ribose, malt dextrin and the like. In one embodiment of the present invention the disaccharide is trehalose dihydrate, the oligosaccharide is fructo-oligosaccharide and the polysaccharide is malt dextrin.

Suitable lipids include, but are not limited to soy bean oil, olive oil, palm kernel oil, peanut oil, walnut oil, cannola oil and the like. Suitable polypeptides include whey protein, egg albumin, gelatin, milk proteins, and other animal and plant proteins. Finally, phytochemicals as used herein include such compounds as polyphenols, saponins, flavanoids, monoterpenes, allyl sulfides, lycopenes, carotenoids, polyactetylenes, silymarin, glycyrrhizin catechins and othethers.

In one embodiment of the present invention the Lactobacillus casei strain KE01 probiotic has the following weight percentage of ingredients:

TABLE 3

| Exemplary Blend | |
|---|---|
| KE01 fine powder | Approximately 1 to 5% |
| Disaccharides | Approximately 25 to 95% |
| Oligosaccharides | Approximately 0 to 10% |
| Polysaccharides | Approximately 0 to 50% |

Preparation of KE01 into Bolus Capsules

Freeze-dried KE01 fine powder (approximately from $10^5$ to $10^{11}$ CFU/g lactobacilli), trehalose dihydrate (Food Grade) and Dextrose (Food Grade) or Malt Dextrin (Grain Processing Corp., Muscatine, Iowa)) were thoroughly blended at 3%: 67%: 30%, respectively. The blended mixture was filled in gelatin capsules. The quality of the KE01 bolus capsules was tested for purity and viability prior to use.

TABLE 4

Exemplary Bolus Blend

| | |
|---|---|
| KE01 fine powder | 3% |
| Trehalose dihydrate (Cargill Foods, Blair, NE) | 67% |
| Malt Dextrin (Grain Processing Corp., Muscatine, IA) | 30% |
| Total | 100% |

Preparation of KE01 in a Gel Form

Freeze-dried KE01 fine powder (approximately from $10^5$ to $10^{11}$ CFU/g lactobacilli) was thoroughly blended with fructo-oligosaccharide (Pharmaceutical Grade) at 2.5% concentration. A non-GMO (Genetically Modified Organism) extruded/expelled soybean oil was used as a primary carrier. The gel is mixed thoroughly, samples were collected from the top, middle, and bottom of the batch using a sterilized spatula and analyzed for purity and viability of the KE01. The KE01 gel was filled into 50/cc tubes for use.

TABLE 5

Exemplary Gel Blend

| | |
|---|---|
| KE01 fine powder | 3% |
| Trehalose dihydrate (Cargill Foods, Blair, NE) | 62% |
| Fructooligosaccharide (Biomatrix, Minneapolis, MN) | 5% |
| Malt Dextrin (Grain Processing Corp., Muscatine, IA) | 30% |
| Total | 100% |

EXAMPLE-2

Cell Adhesion Studies

An in vitro Radio-Adhesion Assay (RAA) was performed to measure the attachment of Lactobacillus strain KE01, using the Cell Environments™ (Becton Dickinson, Bedford, Mass.) 24-well plates containing collagen (Cn) type-I, Cn type-IV, laminin, or fibronectin and using the Caco-2 cell monolayers.

Preparation of KE01 Lactobacilli Cells

A 50 µl inoculum of overnight culture of KE01 grown under anaerobic conditions in Bacto® Lactobacilli MRS broth (Difco) was re-inoculated in 10-ml of MRS broth containing $^3$H-thymidine (20 µci). KE01 cells were grown under anaerobic conditions at 37° C. to exponential phase (approximately 7-hours) to allow optimum uptake and incorporation of $^3$H-thymidine into the bacterial DNA. $^3$H-thymidine labeled KE01 were harvested by centrifugation at 7,500×g, washed and resuspended in phosphate buffered saline (PBS, pH 7.2). The bacterial cell density was optically adjusted to $10^7$ lactobacilli/ml at 600 nm.

Radio-Adhesion Assay (RAA)

For sub-epithelial matrix interaction assays, Cell Environments™ 24-well plates containing collagen (Cn) type-I, Cn type-IV, laminin, or fibronectin were used for testing attachment of KE01. Matrix components were applied as an even, optically clear coating covering a total surface area of 1.75 $cm^2$. Biocoat® Matrigel matrix, a soluble basement membrane extracted from Engelbreth-Holm-Swarm mouse tumor, which when reconstituted at room temperature, forms a gel, was also used in the interaction studies. Two milliliters of KE01 suspension ($2 \times 10^7$ lactobacilli) were added to each well containing matrix layer and incubated at room temperature. After one hour, the KE01 suspension was aspirated from the wells and discarded. One milliliter of trypsin type 1 (110 enzyme units; Sigma Chemicals, St. Louis, Mo.) was added to each well and allowed to hydrolyze for 30 min at room temperature to release the matrix protein layer. The trypsin hydrolysate was aspirated into a scintillation vial and an additional 1 ml from each well was homogenized (Scintigest™; Fisher Scientific, Fair Lawn, N.J.) for 10 min at room temperature. The homogenate was aspirated into the corresponding scintillation vial. A volume of 10-ml scintillation cocktail (ScintiSafe™ Gel, Fisher Scientific) was dispensed into the vial and thoroughly mixed. After settling and clarification of the mixture, the radioactivity was measured using a liquid scintillation analyzer (Tri-Carb 2100 TR®, Packard Inc.).

For eucaryotic cell interaction assays, Caco-2, a colon carcinoma cell line, was grown to confluence as monolayers, in 24-well tissue culture plates, for 72-h in a $CO_2$ incubator using Eagle's minimal essential medium (supplemented with 1% non-essential amino acids and 10% fetal calf serum). After complete monolayers were obtained, each plate was washed twice with phosphate buffered saline (PBS, pH 7.2). A 2-ml volume (approximately $2 \times 10^7$ bacteria) of $^3$H-thymidine labeled lactobacilli suspension was added to each well containing approximately $10^5$ Caco-2 cells. The ratio between Caco-2 cells and lactobacilli was maintained at 1:200. After a 1-hour incubation at 37° C., the bacterial suspension was aspirated and the wells were washed with PBS. Each well was treated with trypsin type 1, tissue homogenizer and measured for radioactivity as described above. Binding was expressed as lactobacilli bound per $cm^2$ area of biological surface (for sub-epithelial matrix protein interactions) or per cell (for Caco-2 cell interactions).

The interaction of KE01 with different biomatrix layers was also compared with the interactions of three ATCC reference strains, *L. casei* ATCC393, *L. reuteri* ATCC23272, and *L. rhamnosus* ATCC 7469 in Table 6. To determine significance, the binding data was analyzed with a 4×6 factorial analysis of variance (SAS Inc., Raleigh, N.C.).

TABLE 6

| BIOMATRIX LAYER | KE01 | *L. Casei* ATCC 393 | *L. reuteri* ATCC23272 | *L. rhamnosus* ATCC7469 |
|---|---|---|---|---|
| Collagen type-I | $7.4 \times 10^6/cm^2$ | $3.5 \times 10^5/cm^2$ | $3.0 \times 10^5/cm^2$ | $4.7 \times 10^5/cm^2$ |
| Collagen type-IV | $5.0 \times 10^6/cm^2$ | $8.7 \times 10^4/cm^2$ | $6.3 \times 10^4/cm^2$ | $9.9 \times 10^4/cm^2$ |
| Laminin | $4.1 \times 10^6/cm^2$ | $6.4 \times 10^4/cm^2$ | $5.3 \times 10^4/cm^2$ | $7.2 \times 10^4/cm^2$ |
| Fibronectin | $5.3 \times 10^6/cm^2$ | $6.4 \times 10^4/cm^2$ | $9.5 \times 10^4/cm^2$ | $1.6 \times 10^4/cm^2$ |
| Matrigel ™ | $6.6 \times 10^6/cm^2$ | $2.1 \times 10^5/cm^2$ | $1.7 \times 10^5/cm^2$ | $2.8 \times 10^5/cm^2$ |
| Caco-2 monolayer | 108/cell | 40/cell | 26/cell | 64/cell |

KE01 demonstrated avid binding to collagen type-I, collagen type-IV, laminin and fibronectin and Matrigel™ layers in vitro. KE01 binding to Caco-2 cell monolayers was approximately 54% (108 lactobacilli/cell). All of the in vitro interactions of KE01 with sub-epithelial matrix layers and Caco-2 cell monolayers were significantly higher than ATCC reference strains, *L. casei* ATCC393 ($p<0.0001$), *L. reuteri* ATCC23272 ($p<0.0001$), and *L. rhamnosus* ATCC7469 ($p<0.0001$).

EXAMPLE-3

Enteric Pathogen Cell Adhesion Interference Studies

The efficacy of KE01 to inhibit the adhesion of enteric pathogens (listed in Table 7) to biomatrices and to detach complexes of pathogen-biomatrices.

TABLE 7

| ENTEROPATHOGEN | SOURCE |
| --- | --- |
| *Escherichia coli* ATCC43888 | Enterotoxigenic isolate that does not produce either Shiga-like toxin (SLT)-I or SLT-II |
| *Escherichia coli* ATCC43889 | Fecal isolate from a patient with hemolytic uremic syndrome that produces SLT-II |
| *Escherichia coli* ATCC43890 | Enterotoxigenic isolate that produces SLT-I |
| *Escherichia coli* ATCC43894 | Fecal isolate from outbreak of hemorrhage colitis that produces both SLT-I and SLT-II |
| *Escherichia coli* ATCC43895 | Isolate from raw hamburger implicated in hemolytic colitis outbreak, known to produce SLT-I and SLI-II |
| *Enterococcus faecalis* ATCC7080 | Isolated from meat involved in food poisoning |
| *Campylobacter coli* ATCC33559 | Isolated from pig feces |
| *Campylobacter jejuni* ATCC29428 | Isolated from diarrheic stool of child. |
| *Salmonella enteritidis* ATCC4931 | Isolated from human gastroenteritis |
| *Salmonella pullorum* ATCC13036 | Isolated from egg |

Adhesion-Detachment Assay

A 10-µl inoculum of overnight culture of *E. coli* O157:H7 grown in tryptic soy broth (TSB) or the other listed pathogens grown in appropriate broth media were re-inoculated in 3-ml of TSB or corresponding appropriate media containing $^3$H-thymidine (20 µci). The binding of bacterial pathogens to Biocoat® plates containing collagen (Cn) type-I, Cn type-IV, laminin, fibronectin and matrigel surfaces was performed as described in Example-1. To these Biocoat®-bacterial pathogen complexes, a 2-ml volume of unlabeled KE01 suspension ($2.0 \times 10^7$ lactobacilli/ml) was added to each well and incubated for 1-h at room temperature. KE01 lactobacilli suspension was aspirated from the well. Following steps of release of contents in the wells and measurement of radioactivity was done according to the protocol described in Example-2. The difference in bacterial cell numbers in wells of adherent pathogens with and without KE01 treatment was expressed as '$Log_{10}$ detachment' values.

Adhesion-Inhibition Assay.

Binding of unlabeled KE01 to Biocoat® plates containing collagen (Cn) type-I, Cn type-IV, laminin, fibronectin and matrigel surfaces was performed as described in Example-2. To these Biocoat®-KE01 complex, a 2-ml volume of $^3$H-thymidine labeled *E. coli* or other bacterial pathogen suspension ($2.0 \times 10^7$ bacteria/ml) was added to each well and incubated for 1-h at room temperature and the suspension was aspirated. Following steps of release of contents in the wells and measurement of radioactivity was done according to the protocol described in Example-2. Biocoate ® wells that were not treated with KE01 served as adhesion controls for *E. coli* or other pathogens. The reduction in attachment of bacterial pathogens to biomatrices that were pretreated with KE01 was expressed as '$Log_{10}$ inhibition' values.

The results of inhibitory and detachment effects of KE01 on *E. coli* O157:H7 (strain ATCC 43895) interactions with biomatrices and Matrigel™ Biocoat surfaces are shown in Table 8.

TABLE 8

| | KE01 EFFECTS ON *E. coli* INTERACTIONS | | |
| --- | --- | --- | --- |
| BIOMATRIX LAYER | *E. coli* bound (bacteria/cm$^2$) | *E. coli*/cm$^2$ ($log_{10}$ Inhibition) | *E. coli*/cm$^2$ ($log_{10}$ Detachment) |
| Collagen type-I | $6.2 \times 10^6$ | $3.3 \times 10^3$ (3.3-log) | $6.7 \times 10^2$ (3.9-log) |
| Collagen type-IV | $2.9 \times 10^5$ | $1.8 \times 10^3$ (2.1-log) | $1.1 \times 10^3$ (2.2-log) |
| Fibronectin | $7.6 \times 10^5$ | $4.4 \times 10^3$ (2.3-log) | $5.8 \times 10^3$ (2.1-log) |
| Laminin | $1.4 \times 10^5$ | $9.2 \times 10^2$ (2.2-log) | $3.7 \times 10^2$ (2.7-log) |
| Matrigel ™ | $9.1 \times 10^6$ | $8.2 \times 10^3$ (3.1-log) | $6.4 \times 10^3$ (3.3-log) |

KE01 demonstrated avid binding to all biosurfaces tested, however, the interaction was significantly higher with collagen type-I and Matrigel™. KE01 caused >3-log inhibition of *E. coli* O157:H7 attachment to collagen type-I and Matrigel™; whereas >2-log inhibition with collagen type-IV, fibronectin and laminin interactions. The efficacy of detachment of adherent *E. coli* by KE01 was in the similar Log magnitudes as inhibition values.

The spectrum of efficacy of KE01 to inhibit binding and to detach adherent bacteria was tested with several enteric pathogens listed in Table 9.

TABLE 9

| | BINDING | STRAIN KE01 EFFECT ON BINDING | |
| --- | --- | --- | --- |
| ENTEROPATHOGEN | (Bacteria/cm$^2$) | $Log_{10}$ Inhibition | $Log_{10}$ Detachment |
| *Escherichia coli* ATCC43888 | $1.9 \times 10^6$ | 3.5-log | 3.8-log |
| *Escherichia coli* ATCC43889 | $9.1 \times 10^6$ | 2.9-log | 3.1-log |
| *Escherichia coli* ATCC43890 | $1.0 \times 10^7$ | 4.2-log | 4.4-log |
| *Escherichia coli* ATCC43894 | $8.4 \times 10^6$ | 3.2-log | 3.2-log |
| *Enterococcus faecalis* ATCC7080 | $2.6 \times 10^6$ | 2.8-log | 3.7-log |
| *Campylobacter coli* ATCC33559 | $7.5 \times 10^6$ | 3.6-log | 3.5-log |
| *Campylobacter jejuni* ATCC29428 | $8.1 \times 10^6$ | 3.3-log | 3.5-log |

TABLE 9-continued

| ENTEROPATHOGEN | BINDING (Bacteria/cm$^2$) | STRAIN KE01 EFFECT ON BINDING | |
|---|---|---|---|
| | | Log$_{10}$ Inhibition | Log$_{10}$ Detachment |
| Salmonella enteritidis ATCC4931 | 3.4 × 10$^7$ | 4.1-log | 3.9-log |
| Salmonella pullorum ATCC13036 | 9.6 × 10$^6$ | 3.9-log | 4.0-log |

KE01 effectively inhibited the interactions of enteropathogens ranging from 2.8-log (with *Enterococcus faecalis*) to 4.2-log (with *Salmonella enteritidis*). Comparatively, the efficacy of KE01 to detach enteropathogens was higher ranging from 3.1-log (with enterohemorrhagic *E. coli* ATCC43889) to 4.4-log (with enterohemorrhagic *E. coli* ATCC43890).

EXAMPLE-4

The Efficacy of KE01 Fine Powder to Detach Adherent Enteric Pathogens

The efficacy of KE01 fine powder to detach adherent enteric pathogens was tested in a cellular system using Caco-2 monolayers. The Caco-2 cell adhesion assay for enteropathogens was performed as described for KE01 in Example 2. The adhesion-detachment assay was performed as described for Biomatrix layers in Example 3. However, in the above two protocols KE01 powder was used as a 1% solution (1-g fine powder suspended and thoroughly vortexed in 100-ml physiological saline, pH 7.2). Treatment with physiological saline was used as control and the value was subtracted as background while interpreting the result. The data is shown in Table 10.

TABLE 10

| ENTEROPATHOGEN | UNTREATED Bacteria/well (/cell) | KE01-TREATED Bacteria/well (/cell) | DETACHMENT Log$_{10}$ (%) |
|---|---|---|---|
| Escherichia coli ATCC43888 | 1.1 × 10$^6$ (15) | 7.3 × 10$^4$ (0.97) | 1.3-log (93.5%) |
| Escherichia coli ATCC43889 | 5.1 × 10$^6$ (68) | 2.2 × 10$^4$ (0.29) | 2.3-log (99.6%) |
| Escherichia coli ATCC43890 | 5.7 × 10$^6$ (76) | 8.3 × 10$^3$ (0.11) | 2.7-log (99.8%) |
| Escherichia coli ATCC43894 | 4.8 × 10$^6$ (64) | 1.9 × 10$^4$ (0.25) | 2.3-log (99.6%) |
| Escherichia coli ATCC43895 | 6.2 × 10$^6$ (83) | 3.8 × 10$^4$ (0.51) | 2.2-log (99.4%) |
| Enterococcus faecalis ATCC7080 | 1.9 × 10$^6$ (22) | 5.5 × 10$^4$ (0.73) | 1.6-log (96.7%) |
| Campylobacter coli ATCC33559 | 4.3 × 10$^6$ (57) | 7.1 × 10$^4$ (0.95) | 1.7-log (98.3%) |
| Campylobacter jejuni ATCC29428 | 4.1 × 10$^6$ (55) | 6.5 × 10$^4$ (0.87) | 1.8-log (98.4%) |
| Salmonella enteritidis ATCC4931 | 6.6 × 10$^6$ (88) | 8.3 × 10$^3$ (0.11) | 2.8-log (99.9%) |
| Salmonella pullorum ATCC13036 | 6.7 × 10$^6$ (89) | 7.9 × 10$^3$ (0.10) | 3.1-log (99.9%) |

The Caco-2 cell adhesion profiles of enteropathogens were ranging from 1.1×10$^6$ (15 bacteria per Caco-2 cell with enterohemorrhagic *E. coli* ATCC43888) to 6.7×10$^6$ (89 bacteria per Caco-2 cell with *Salmonella pullorum* ATCC13036). KE01 has effectively dissociated the Caco-2 cell adherent enteropathogen complexes with the detachment efficacy ranging from 1.3-log (93.5%) to 3.1-log (99.9%) for *E. coli* ATCC43888 and *Salmonella pullorum*, respectively.

EXAMPLE-5

Demonstration of the Ability of Fresh and Freeze-Dried KE01 Preparations to Adhere and Colonize the Epithelial Mucosa of the Bovine Intestinal Tract Bovine Intestinal Adhesion Assay Intestine samples were obtained from freshly slaughtered animals and transported to the laboratory in refrigerated conditions. Intestines were cut-open and epithelial mucosa of the lumen was gently washed to remove fecal debris. Two different preparations of KE01 was inoculated on a 1 inch$^2$ mucosal surface, A) $^3$H-thymidine labeled KE01 described in Example 2 (0.1 ml inoculum containing approximately 10$^7$ lactobacilli); and B) KE01 powder blend mixture described in Example 1 (homogenously suspended in physiological saline and diluted, 0.1 ml inoculum containing approximately 10$^7$ lactobacilli). After 2-h incubation, the area of inoculum was gently washed three times with physiological saline.

Sample Preparation-A, was examined for KE01 attachment. The area of inoculum was excised, digested with tissue homogenizer, amplified with liquid scintillation fluid and the radioactivity was measured according to the Radio-Adhesion assay as described in Example-2. KE01 demonstrated avid binding to bovine intestinal epithelial mucosa i.e. approximately 2.5×10$^6$ lactobacilli/inch$^2$.

Figure 3:
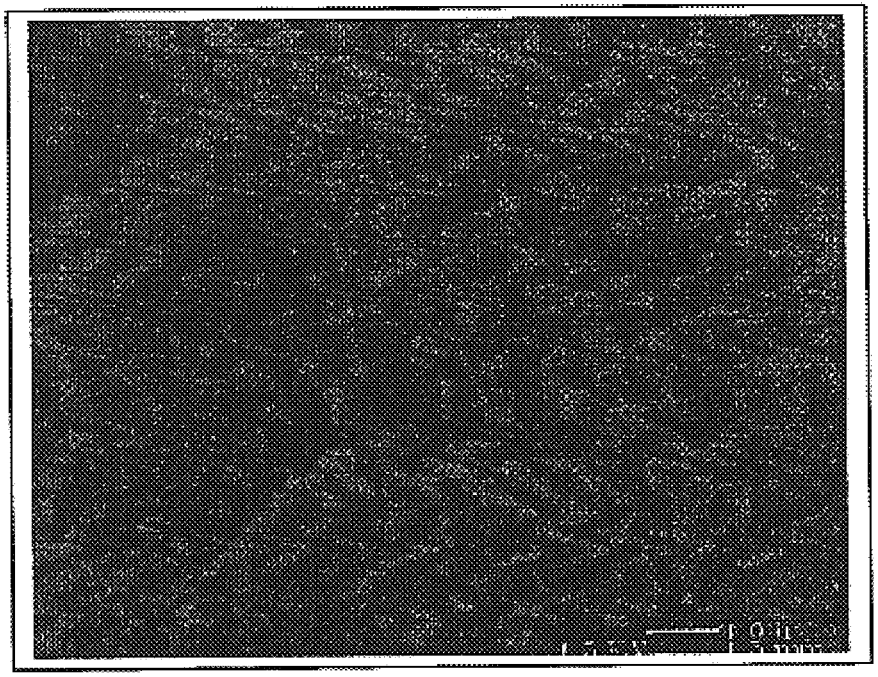
FIG. 3 depicts the attachment of Lactobacillus casei strain KE01 to bovine intestinal epithelia.
Figure 4:
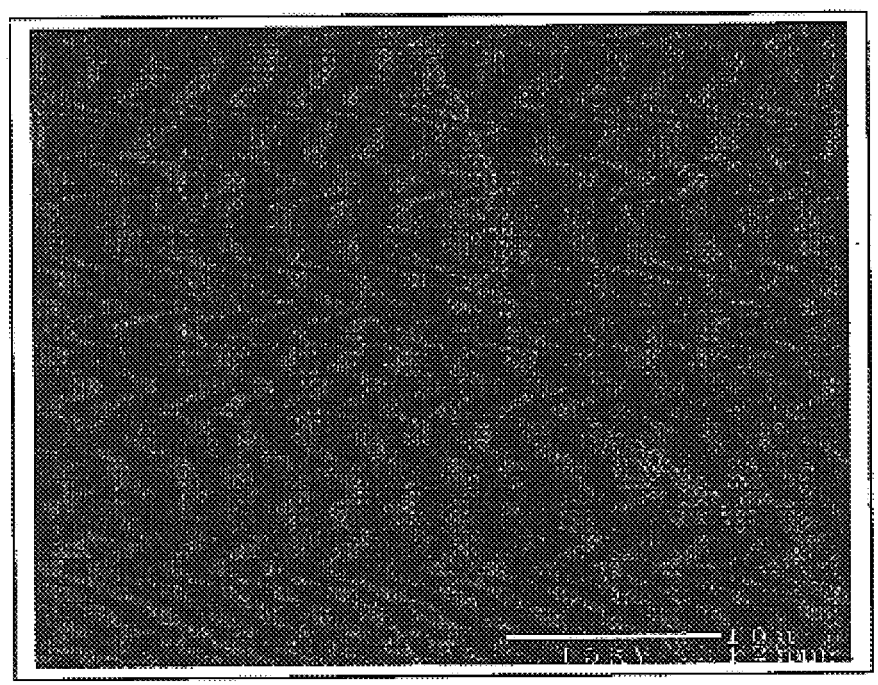
FIG. 4 depicts the colonization formed biofilm on the bovine intestinal epithelial mucosa.

Sample Preparation-B, was evaluated for KE01 colonization by scanning electron microscopy (SEM). Specimens were treated with 2% OsO4 for 30–60 min and rinsed with water. Specimens were treated with 50%, 70% and 95% ethanol, each for 5 min, followed by 2×10 min rinses with 100% ethanol. After critical point drying with liquid carbon dioxide, specimens were mounted and sputter coated with gold palladium. The biopsy specimens were examined using a JEOL6300 scanning electron microscope. The microscopic observations are shown in FIGS. 3 & 4.

EXAMPLE-6

In vivo Probiotic Effects of KE01 Containing Animal Feed-Supplements Administered to Piglets. Demonstration of Intestinal Colonization and Fecal Shedding of KE01; Ability of KE01 to Decrease Porcine Fecal Odor (Reduction of Fecal Sulfide and Ammonia Content); and KE01 Contribution to Weight Gains of the Animal Feed-Supplement Dosage Feed-supplement dosages were prepared in a gel-form as described in Example-1. Briefly, freeze-dried KE01 fine powder (approximately from $10^5$ to $10^{11}$ CFU/g lactobacilli) was thoroughly blended with fructo-oligosaccharide (FOS) at 2.5% concentration. A non-GMO (Genetically Modified Organism) extruded/expelled soybean oil was used as a primary carrier. The gel is mixed thoroughly, samples were collected from the top, middle, and bottom of the batch using a sterilized spatula and analyzed for purity and viability of the KE01. The KE01 gel was filled into 50/cc tubes for use. Control feed dosages containing carrier alone, carrier blended with KE01 cells and carrier blended with KE01 cells and FOS, were also prepared.

Animal Feed-Supplement Trial

The study included a total of 20 pigs (between 6–8 week old) weighing in the range of 40–60 lbs. These animals were divided into four Groups, each comprising of 5 animals, categorized as the following:

Group-1 (Control): Animals fed with 10 cc of gel containing primary carrier only.

Group-2: Animals fed daily with 10 cc of gel containing only 2.5% FOS blended with the primary carrier.

Group-3: Animals fed daily with 10 cc of gel containing about $10^{10}$ cfu/cc of strain KE01 cells only, blended with the primary carrier.

Group-4: Animals fed daily with 10 cc of gel containing a combination of $10^{10}$ cfu/cc of strain KE01 cells and 2.5% FOS, blended with the primary carrier.

Animals were separated by group and contained in isolated penns and were regularly fed with high-protein porcine diet. The four groups of animals were fed daily with 10 cc of their respective category of dietary-supplement dosage. The experiment was conducted for a duration of 6 weeks. Fecal analysis and body weight measurements were regularly performed every week throughout the feed-supplement trial.

Feces Collection

Fecal samples (approximately 20 g per animal) were collected in sterile 50 cc polystyrene tubes. Samples were diluted at 1:1 w/v ratio in normal saline, thoroughly homogenized on a vortex blender, and centrifuged at 2K×g for 5 min. The supernatant was carefully decanted and subjected to microbiological and chemical analysis.

Fecal samples were collected one day prior to the actual feed-supplement trial to obtain a baseline microbiological count (fecal coliforms and fecal lactobacilli), and a baseline level of fecal ammonia and fecal sulfide content.

Microbiological Analysis of Feces

The fecal solution (1:1 w/v decanted supernatant) was serially diluted by 10-fold in normal saline. Selected dilutions were plated in duplicate on MRS agar (Difco) for total lactobacilli counts, and on MacConkey Agar (Difco) for total coliforms counts, using an Autoplate® 4000 device (Spiral Biotech, Norwood, Mass.). The plating was performed in a exponential log dilution setting on the spiral autoplater. Agar plates were incubated at 37° C. for MacConkey agar and 32° C. for MRS agar for 24 to 48 hrs, respectively. The total colony counts were estimated using an automated infra-red Q-count device (Spiral Biotech, Norwood, Mass.). Data were expressed as bacteria per gm of feces and the results were shown for lactobacilli counts in FIG. 5 and fecal coliforms counts in FIG. 6.

Figure 5:
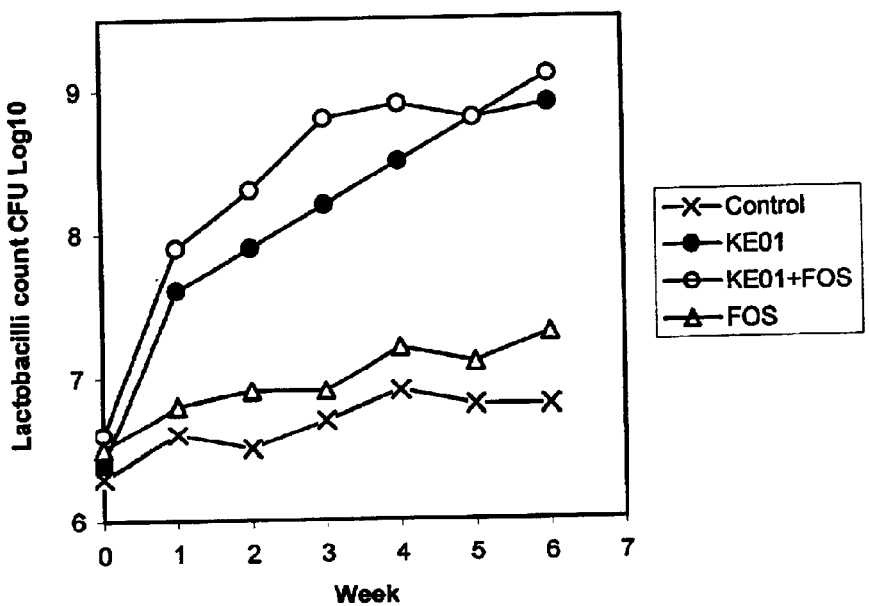
FIG. 5 graphically depicts the enhanced gut colonization and fecal shedding of lactobacilli and as a result of supplementing the animal's diet with Lactobacillus casei strain KE01 in accordance with the teachings of the present invention.
Figure 6:
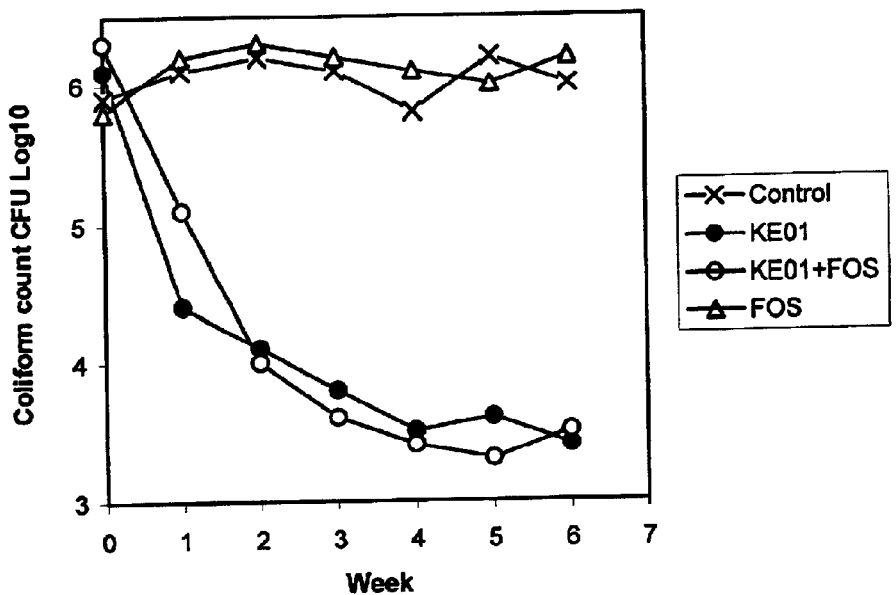
FIG. 6 graphically depicts the reduction of fecal coliform counts as a result of supplementing the animal's diet with Lactobacillus casei strain KE01 in accordance with the teachings of the present invention.

Animals administered with feed-supplements containing KE01 and combination of KE01 plus FOS showed about 2.5-log increase in fecal shedding of lactobacilli compared to control groups, indicating proliferation and colonization of strain KE01 in the porcine gastrointestinal tract as shown in FIG. 5. On the otherhand, fecal coliforms counts decreased by about 2.5-log in KE01 and KE01+FOS fed animals compared to control animals indicating an effective competitive exclusion by strain KE01 in the porcine gut as shown in FIG. 6.

Sulfide and Ammonia Analysis of Feces

Sulfide and ammonia levels in the feces were measured with ion-selective electrodes using a MP230 pH/Ion meter (Mettler Toledo, Columbus, Ohio).

For standardization of a sulfide ion-selective electrode, a 75-ml dilute sulfide standard (10 ppm) solution was added under gentle stirring, to 25-ml sulfide antioxidant buffer. The electrode potential ($E_1$) of the solution was measured using a DX232 silver selective electrode combined with a DX200 reference electrode. The $E_2$ was measured separately with 75-ml sulfide (100 ppm) solution and 25-ml sulfide antioxidant buffer. The differences between $E_1$ and $E_2$ constituted the slope for the sulfide electrode. For sample measurement, a 100-ml of standard (100 ppm) silver solution was mixed with 2-ml of bromide ISA (ionic strength adjustment) buffer and the $E_1$ value was measured. The $E_2$ value was measured by mixing a 10-ml of fecal solution to the above solution. The difference between $E_1$ and $E_2$ was considered $\Delta E$. Based on the standard slope and $\Delta E$, the concentration of sulfide in the feces was estimated according to the concentration ratio (Q) chart using the equation, $C = C_s \times Q$ (C=sulfide conc. in feces; $C_s$=known sulfide conc. i.e. 100 ppm standard; and Q=concentration ratio).

For standardization of the ammonia ion-selective electrode, a 1-ml ammonia standard (1000 ppm) solution was added under gentle stirring, to 100-ml distilled water premixed with 2-ml ammonia pH/ISA (ionic strength adjustment) buffer. The electrode potential ($E_1$) of the solution was measured using ammonia DX217 electrode. The solution was then spiked with 10-ml ammonia (1000 ppm) standard and the change in the electrode potential ($E_2$) was measured. The difference between $E_1$ and $E_2$ constituted the slope for the ammonia electrode. For sample measurement, a 10-ml of fecal solution was added, under gentle stirring to 90-ml distilled water premixed with 2-ml ammonia pH/ISA buffer and the $E_1$ was measured. The fecal solution was spiked with ammonia standard and the $E_2$ was measured. The concentration of ammonia in the feces was estimated using the equation as above.

Figure 7:
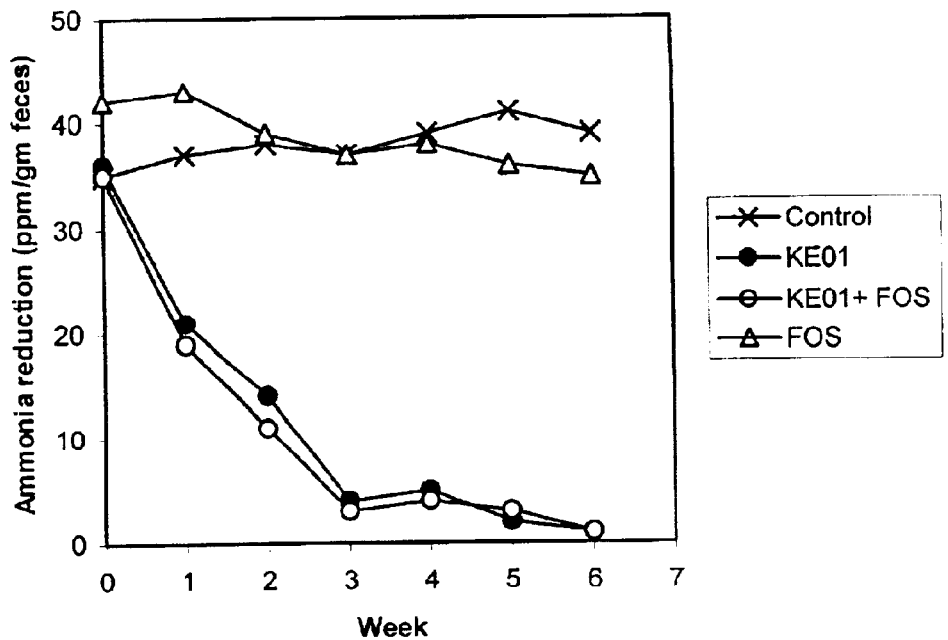
FIG. 7 graphically depicts the reduction in ammonia products in animal feces as a result of supplementing the animal's diet with Lactobacillus casei strain KE01 in accordance with the teachings of the present invention.
Figure 8:
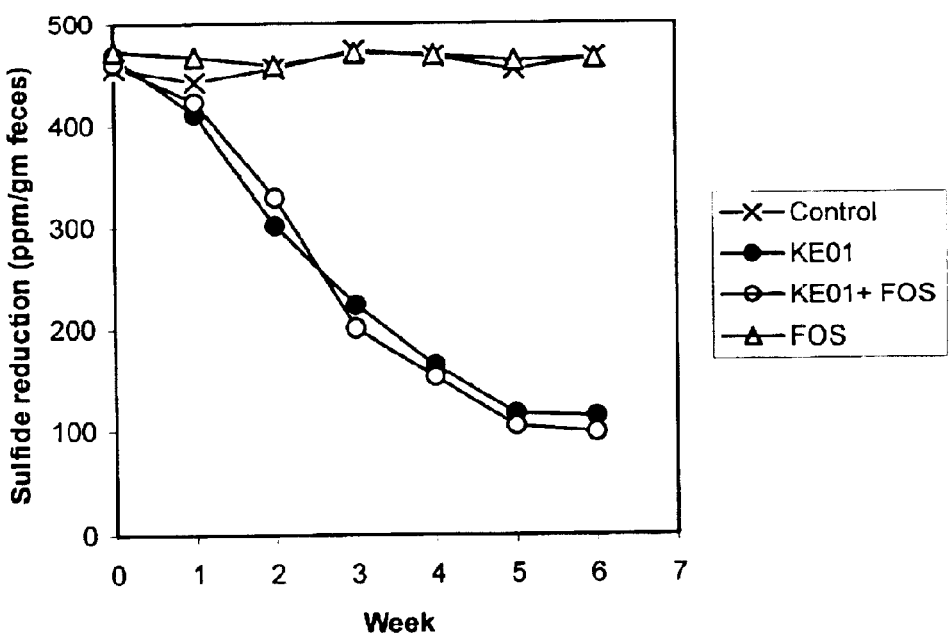
FIG. 8 graphically depicts the reduction in sulfide products in animal feces as a result of supplementing the animal's diet with Lactobacillus casei strain KE01 in accordance with the teachings of the present invention FIG. 9 graphically depicts the increase in weight gains in animals as a result of supplementing the animal's diet with Lactobacillus casei strain KE01 in accordance with the teachings of the present invention.

Animals administered feed-supplement containing KE01 and KE01 plus FOS demonstrated a marked reduction of ammonia by about 35 ppm/gm and of sulfide by about 375 ppm/gm compared to control group of animals as shown in FIGS. 7 & 8. Also the feces from animals fed with KE01 and KE01 plus FOS are rancid due to lactic acid production by the proliferating probiotic KE01 lactobacilli.

Animal Body-Weight Gain Measurements

Figure 9:
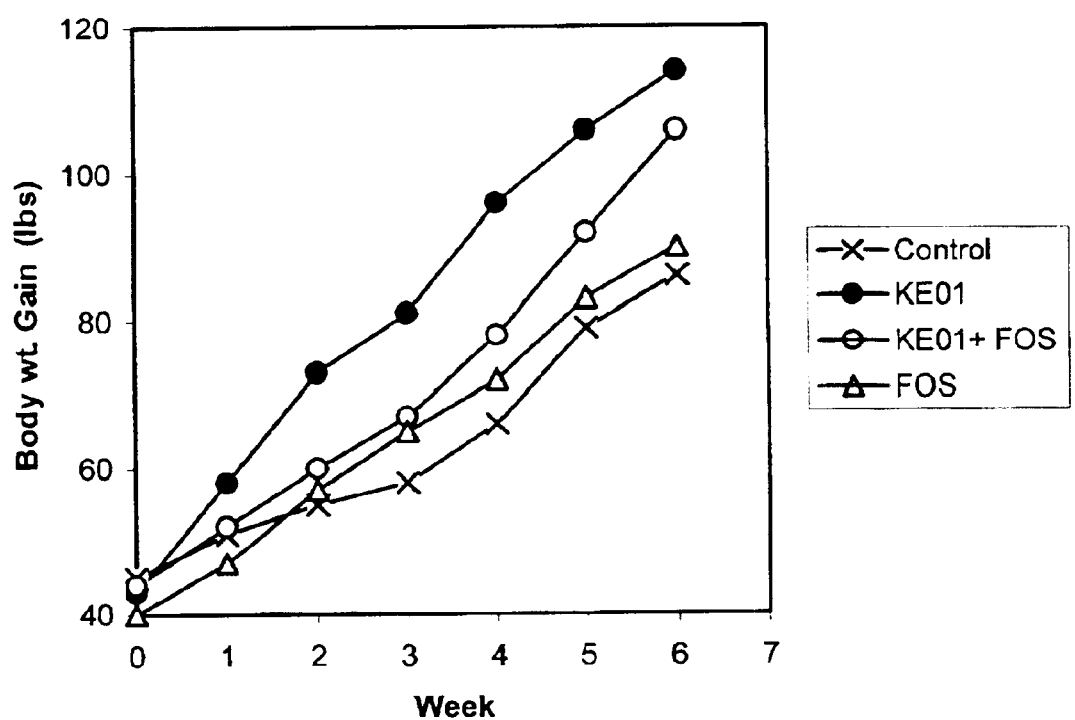

Animals were weighed one day prior to the actual feed-supplement trial to obtain baseline measurements for body weight gains. The body weights of animals from all the four groups were measured once every week though out the 6-week feed trial. At the conclusion of the experiment, animals fed with KE01 showed a body weight gain of about 28 lbs, and the animal group that received KE01 plus FOS showed a body weight gain of 20 lbs compared to control group of animals as depicted in FIG. 9.

III. Conclusion

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference.

What is claimed is:

1. A probiotic composition comprising biologically pure culture of *Lactobacillus casei* strain KE01 having ATCC accession number PTA-3945, *Lactobacillus casei* strain KE01 is derived from a biologically pure culture.

2. The probiotic composition according to claim 1 further comprising inert or active ingredients selected from the group consisting of carbohydrates, polypeptides, lipids, phytochemicals and combinations thereof.

3. The probiotic composition according to claim 2 wherein said carbohydrate is selected from the group consisting of monosaccharides, disaccharides, oligosaccharides, polysaccharides and combinations thereof.

4. The probiotic composition according to claim 3 wherein said carbohydrate is selected from the group consisting of trehalose, maltose, sucrose, dextrose, lactose, inulin, ribose and combinations thereof.

5. The probiotic composition according to claim 3 wherein said disaccharide is trehalose dihyradrate.

6. The probiotic composition according to claim 3 wherein said oligosaccharide is fructo-oligosaccharide.

7. The probiotic composition according to claim 3 wherein said polysaccharide is malt dextrin.

8. The probiotic composition according to claim 2 wherein said polypeptide is selected from the group consisting of whey protein, egg albumin, gelatin, milk proteins, and combinations thereof.

9. The probiotic composition according to claim 2 wherein said lipid is selected from the group consisting of soy bean oil, olive oil, palm kernel oil, peanut oil, walnut oil, cannola oil and combinations thereof.

10. The probiotic composition according to claim 2 wherein said phytochemical is selected from the group consisting of polyphenols, saponins, flavanoids, monoterpenes, allyl sulfides, lycopenes, carotenoids, polyactetylenes, silymarin, glycyrrhizin catechins and combinations thereof.

11. The probiotic composition according to claim 1 further comprising trehalose.

12. The probiotic composition according to claim 11 further comprising malt dextrin.

13. The probiotic composition according to claim 11 further comprising fructo-oligosaccharide.

14. The probiotic composition according to clam 13 wherein said *Lactobacilli casei* strain KE01 is present in the amount of approximately 105 to 1011 colony forming units (CFU) per gram.

15. The probiotic composition according to any one of claims 1 through 14 wherein said probiotic composition is a bolus, gel or liquid that is administered to an animal.

16. The probiotic composition according to claim 15 wherein in said animal is selected from the group consisting of mammals, fish, birds, and reptiles.

17. The probiotic composition according to claim 16 wherein said mammal is selected from the group consisting of humans, horses, dogs, cats, rabbits, sheep, swine, and cows.

18. The probiotic composition according to claim 16 wherein said bird is selected from the group consisting of chickens, turkeys, pheasants, quail, parakeets, and parrots.

19. The probiotic composition according to claim 15 wherein said bolus is selected from the group consisting of gelatin capsules, pressed tablets, and gel caps.

20. The probiotic composition according to claim 19 wherein said bolus is packaged in a polymer-lined foil pouch.

21. A probiotic composition comprising:
    powdered *Lactobacillus casei* strain KE01 having ATCC accession number PTA-3945 in the amount of from approximately 1 to 5 weight percent;
    a disaccharide form approximately 25 to 95 weight percent;
    an oligosaccharide from approximately 0 to 10 weight percent; and
    a polysaccharide from approximately 0 to 50 weight percent.

22. The probiotic composition of claim 21 wherein said powdered *Lactobacillus casei* strain KE01 having ATCC accession number PTA-3945 has approximately 105 to 1011 CFU per gram and is present in the amount of approximately 3 weight percent.

23. The probiotic composition of claim 21 wherein said disaccharide is present in the amount of approximately 62 weight percent.

24. The probiotic composition of claim 21 wherein said oligosaccharide is present in the amount of approximately 5 weight percent.

25. The probiotic composition of claim 21 wherein said polysaccharide is present in the amount of approximately 30 weight percent.

26. The probiotic composition of claim 21 wherein said disaccharide is trehalose, said oligosaccharide is fructo-oligosaccharide and said polysaccharide is malt dextrin.

27. A probiotic composition comprising:
approximately 3 weight percent of powdered *Lactobacillus casei* strain KE01 having ATCC accession number PTA-3945 having approximately 105 to 1011 CFU per gram;
approximately 62 weight percent trehalose;
approximately 5 weight percent fructo-oligosaccharide; and
approximately 30 weight percent malt dextrin.

28. A method of inhibiting enteric pathogen disease in an animal comprising:
orally administering an effective amount of the probiotic compositions according to any one of claims 1, 11, 12, 13, 20 or 26 to an animal in need thereof.

29. The method according to claim 28 wherein said enteric pathogen is selected from the group consisting of enteropathogenic *Escherichia coli* (EPEC), enterotoxigeneic *E. coli* (ETEC), *Salmonella enteriditis*, *Yersina pseudotuberculosis* and *Listeria monocytogenes*.

30. The method according to claim 28 wherein said animal is selected from the group consisting of mammals, fish, birds, and reptiles.

31. The method according to claim 30 wherein said mammal is selected from the group consisting of humans, horses, dogs, cats, rabbits, sheep, swine, and cows.

32. The method according to claim 30 wherein said bird is selected from the group consisting of chickens, turkeys, pheasants, quail, parakeets, and parrots.

33. The method according to claim 28 wherein said administering step further comprises a probiotic compositions selected from the group consisting of gelatin capsules, pressed tablets, gel caps, animal feed and liquid beverages.

* * * * *

UNITED STATES PATENT AND TRADEMARK OFFICE
CERTIFICATE OF CORRECTION

PATENT NO.       : 6,797,266 B2
APPLICATION NO.  : 10/021871
DATED            : September 28, 2004
INVENTOR(S)      : A. Satyanarayan Naidu It is certified that error appears in the above-identified patent and that said Letters Patent is hereby corrected as shown below:

In the claims, claim 1, column 23, line 50, replace the text beginning with "1. A probiotic composition" and ending "biologically pure culture." with the following claim:

1. A probiotic composition comprising a biologically pure culture of Lactobacillus casei strain KE01 having a ATCC accession number PTA-3945.

Signed and Sealed this

Ninth Day of January, 2007

JON W. DUDAS
*Director of the United States Patent and Trademark Office*